(12) United States Patent
Jin et al.

(10) Patent No.: US 7,162,089 B2
(45) Date of Patent: Jan. 9, 2007

(54) METHOD FOR SEGMENTING AND RECOGNIZING AN IMAGE IN INDUSTRY RADIATION IMAGING

(75) Inventors: Hui Jin, Beijing (CN); Li Zhang, Beijing (CN); Zhiqiang Chen, Beijing (CN); Jianping Cheng, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 627 days.

(21) Appl. No.: 10/297,845

(22) PCT Filed: Apr. 12, 2002

(86) PCT No.: PCT/CN02/00257

§ 371 (c)(1),
(2), (4) Date: Jun. 2, 2003

(87) PCT Pub. No.: WO02/084268

PCT Pub. Date: Oct. 24, 2002

(65) Prior Publication Data

US 2004/0091151 A1 May 13, 2004

(51) Int. Cl.
*G06K 9/48* (2006.01)
*G06K 9/56* (2006.01)

(52) U.S. Cl. ..................... 382/199; 382/205
(58) Field of Classification Search .................. None
See application file for complete search history.

(56) References Cited

U.S. PATENT DOCUMENTS

| | | | |
|---|---|---|---|
| 4,910,786 A | 3/1990 | Eichel | |
| 5,319,547 A | 6/1994 | Krug et al. | |
| 6,021,222 A | 2/2000 | Yamagata | |
| 6,055,337 A * | 4/2000 | Kim | 382/242 |
| 6,728,404 B1 * | 4/2004 | Ono et al. | 382/190 |
| 6,987,535 B1 * | 1/2006 | Matsugu et al. | 348/239 |
| 2002/0012464 A1 * | 1/2002 | Han et al. | 382/199 |

OTHER PUBLICATIONS

SHUI, Zheng Yuan, et al. "Nuclear Electronics & Detection Technology", vol. 16 No. 2, Mar. 1996.
"On the Encoding of Arbitrary Geometric Configurations", by Herbert Freeman, IRE Transactuis i Electronic Computers, pp. 260-268.
"Segmentation of Handguns in Dual Energy X-ray Imagery of Passenger Carry-on Baggage", by R. Paranjape, et al., IEEE, 1998, pp. 377-380.

* cited by examiner

*Primary Examiner*—Jingge Wu
*Assistant Examiner*—Charles Kim
(74) *Attorney, Agent, or Firm*—Birch, Stewart, Kolasch & Birch, LLP

(57) ABSTRACT

An image segmentational recognition method in industrial radiational imaging, comprising the steps of: pre-processing an original image to climate noises; log-transforming, to obtain a linear attenuation coefficient image; edge detecting; edge tracking, to track the points whose edge values are close to each other to obtain edge segments; edge connecting, to connect edge segments; edge connecting, to connect edge segments whose average edge values are close to each other; edge closing; region filling; and region displaying. In comparison with existing arts, the present invention can separate effectively the overlapped objects in an image, raise the efficiency of image inspection, and find out concealed contraband goods more easily.

8 Claims, 4 Drawing Sheets

METHOD FOR SEGMENTING AND RECOGNIZING AN IMAGE IN INDUSTRY RADIATION IMAGING

The present invention relates to the image processing in industrial radiational imaging, particularly, to an image segmentation recognition method in industrial radiational imaging.

In prior art, the image segmentation recognition is mostly used in medical image processing, and these methods have assumed that the linear attenuation coefficients of objects on an image are distributed uniformly and the objects are not overlapped with each other. For industrial radiational imaging, especially in goods inspection systems, however, the objects on an image are often overlapped with each other, so the medical image processing methods can not be used in such cases. Recently, a new method is developed, which is based mainly on direction data of edges, and uses a so-called edge extension assumption to deal with the overlapped objects on a gray level image taken with conventional photography. But these methods can only segment some very simply overlapped objects, and when used to various complicated objects in industrial radiational imaging, the segmenting results are not satisfied and the time consumed is long, thus these methods have no application value in this case.

Considering the problems existing in the prior art, the object of present invention is to provide an image segmentation recognition method in industrial radiational imaging. It can discriminate automatically the different objects on a ratiational image from each other and display them separately. In particular, it can separate the overlapped objects in an image effectively to improve the image detection efficiency and to find out concealed contraband goods more easily.

To achieve the above object present invention provide an image segmentational recognition method in industrial radiational imaging, the method comprises the steps of (1) Pre-processing an original image to reduce. the influence of noises, denoting a gray level value of a pixel at (x,y) with G (x,y); (2) Log-transforming the image pre-processed to obtain a linear attenuation coefficient image, that is, A(x,y) =C ln (G(x,y)/Io)+Ao, where Io=Ao is the maximum gray level value of the image, C is a constant used for adjusting the contrast; (3) Performing an edge detection on the linear attenuation coefficient image A(x,y) to obtain an edge value image E(x,y) and an edge direction image D(x,y); (4) Refining the edges by using the edge value image E(x,y) and edge direction image D(x,y), to create a new edge value image EN(x,y); (5) Performing and edge tracking operation by using the edge value image EN(x,y) and edge direction image D(x,y), calculating an average value for each edge segment obtained by the edge tracking operation, for each edge point on each edge segment, searching other edge points on other neighboring edge segments; if such an edge point is found, calculating a difference between the average edge values of the two edge segments; when the difference is located within the preset narrow range, determining logically the two edge segments to belong to a same edge, (6) For each edge point on the edge segments logically determined to belong to a same edge, searching for its adjacent points on the same-edge segments logically determined to belong to a same edge. If there is one or more gaps between the edge point and its adjacent points, filling the gaps to close the edge, thus forming a complete contour of an object; (7) Checking whether all points in the image belong to the object, and marking all points belonging to the object; (8) Cutting off false filled-regions; and (9) Creating a region as an isolated object by combining a closed edge and filling points.

In an embodiment of present invention, said pre-processing for an original image in step (1) may be performed using a Gaussian low-pass filtering in spatial domain.

In an embodiment of present invention, said process far edge detection in step (3) includes the following steps: at a 3*3 neighboring region of each candidate pixel (x,y), find out gradient values in 8 directions respectively by using a kirsh operator, the maximum gradient value therein is the edge value E (x,y) at that pixel, and the corresponding direction thereof is the edge direction D(x,y).

In an embodiment of present invention, said process for refining the edges in step (4) may comprises the steps of 1) initial refining, that is by finding out peak value points on the edge value image to create a new edge value image E' (x,y); 2) Further refining the initial refined edge value image E, (x,y) based on an iteration algorithm for sequential morphological refining, to erase redundant edge points repeatedly in 8 directions of east, south-east, south, south-west, west, north-west, north, and north-east, until the image can not be further refined, and thus to create a new edge value image EN(x,y).

In an embodiment of present invention, the process of cutting off false filled regions may be performed by using a method of region growing.

In an embodiment of present invention, a criterion for said checking in step (7) may be that all points in the image are checked and if a checked edge points of a same object exist in all 4 directions of top, down, left and right of a point, then the checked point is determined to belong to the object.

In an embodiment of present invention, the said process for edge tracking in step (5) comprises the following steps: 1) For each edge point which has not been determined to belong to any known edge, searching one or more edge points in its 3*3 neighboring region according to a principle of having priority in edge direction, and if an edge searched point which has such an edge value that the difference between the value of said each edge point and the edge value is located within a preset narrow range and does not belong to any known edge is found, then determining these two points belong to a new edge, so taking this point searched as a new starting point, while if no new starting point is found when all points have been searched, then stopping the edge tracking operation; 2) Setting the new starting point as a current edge point, by using a method similar to that in step 1), searching for a next adjacent edge point in its neighboring regions being 3*3, 5*5 till 7*7, and if the next adjacent edge point is found, taking it as the current edge point and repeating step 2), while if no such a point is found. Then the searching operation for current edge is ended and turning to step 1) to search a next edge.

In an embodiment of present invention, the said process for edge connection comprises the following steps: 1) Calculating An average edge value for each edge; 2) Searching in neighboring regions being 3*3, 5*5, till 9*9 for each edge point, if it is found that a point belongs to another a edge and the difference between the average edge values of the two edges is located within a preset narrow range, then the two edges belong to a same object, so performing an edge combination operation to obtain a new edge and calculating an average edge value of the new edge; 3) After the searching operation for all points is ended, and if any edge combination occurs, then repeating step 2), otherwise stopping the edge connection operation.

In comparison with prior art, present invention can track the edges of

In comparison with prior art, present invention can track the edges of an object having substantially same linear attenuation coefficients in an image and connect them with each other, and can discriminate effectively different objects, which have different linear attenuation coefficients but are over lapped with each other, from each other, and display them respectively. The segmentation results for objects not overlapped with each other will be even better. Thus the efficiency of image inspection may be improved and the concealed contraband goods may be found more easily.

These and other advantages of the present invention will become apparent to those skilled in the art upon reading and understanding the following detailed description with reference to the accompanying figures.

Figure 1:
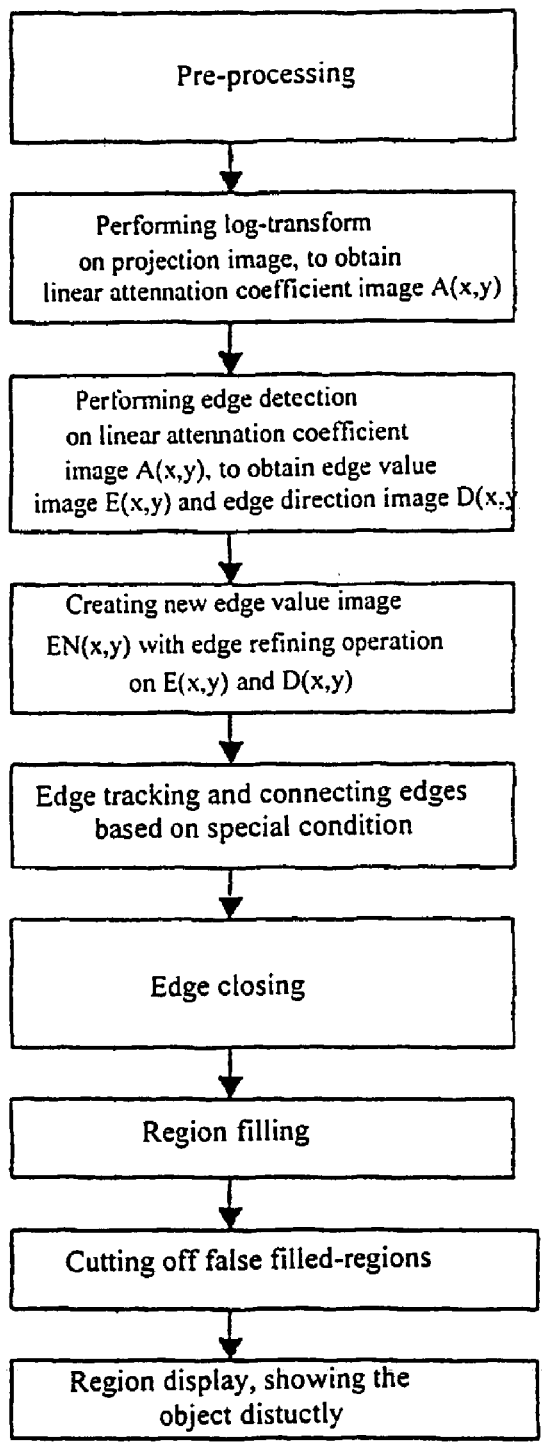
FIG. 1 is a flow-chart showing the steps of a method in accordance with present invention.

Now refer to FIG. 1, illustrating a flow chart of an image segmentation recognition method in industrial radiational imaging according to present invention is shown. In particular, speaking, the method includes the following nine step (1) to (9). The process in step (1) include: performing a pre-processing on an original image to reduce the influence of noise, and denoting the gray level value at a pixel (x,y) with G(x,y); According to an embodiment of present invention, a Gaussian low-pass filter in spatial domain may be used to filter the original image to reduce the noises in the original image effectively, or other types of filters may also be used to reduce the influence of noise in original image.

The process in step (2) includes: performing a log-transform operation on a project image to obtain a linear attenuation coefficient image, that is A (x,y)=C lN(G(x,y)/Io)+Ao, where Io=Ao is the maximum gray level value of the image, C is a constant used for adjusting the contrast.

Figure 2:
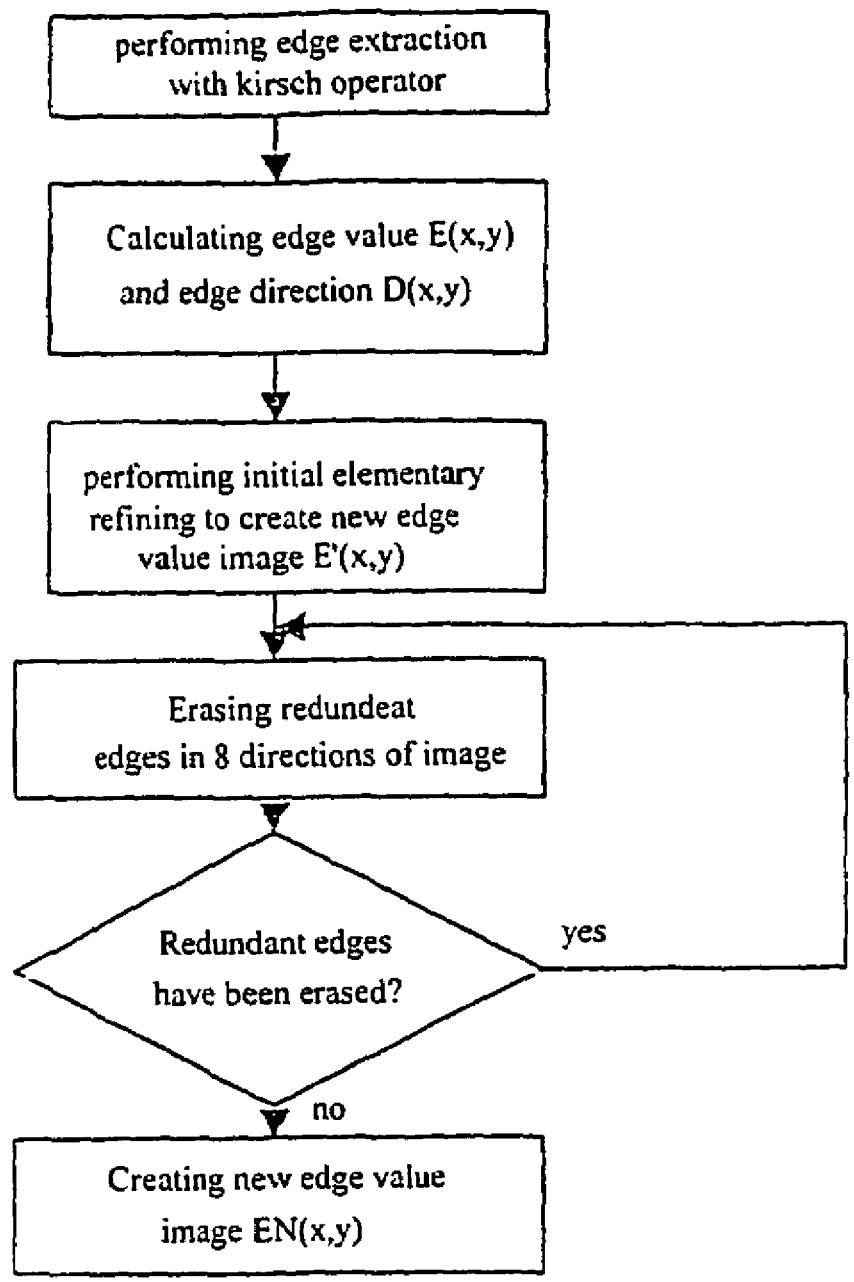
FIG. 2 is a flow-chart showing the steps of the edge detection and edge refining operations in accordance with present invention.

The process in step (3) includes: performing an edge detection on the linear attenuation coefficient image A(x,y) to obtain an edge value image E(x,y) and an edge direction image D(x,y). Refer to FIG. 2 illustrating a specific method for performing said edge detection operation in step (3), the method includes following steps: by the use of kirsch operator, calculating the gradient values in 8 directions respectively in a 3*3 neighboring region of each candidate pixel (x,y), wherein the maximum value of 8 gradient values is the edge value E(x,y) at the pixel, and a corresponding direction thereof is the edge direction D(x,y), wherein the said edge refining operation in step (4) has the following steps: 1) Initial refining, in particular, by finding out peak value points in the edge value image to create a new edge value image E'(x,y); 2) Further refining the new edge value image E'(x,y) by the use of a method of image morphology, that is by using an iteration algorithm for sequential morphological refining to erase the redundant edge points repeatedly in 8 directions of east, south-east, south, south-west, west, north-west, north and north-east, until the image can not further be refined, and thus to create a new edge value image EN(x,y).

The process in step (4) includes: performing an edge refining operation based on the edge value image E(x,y) and the edge direction image D(x,y) to create a new edge value image EN(x,y).

Figure 3:
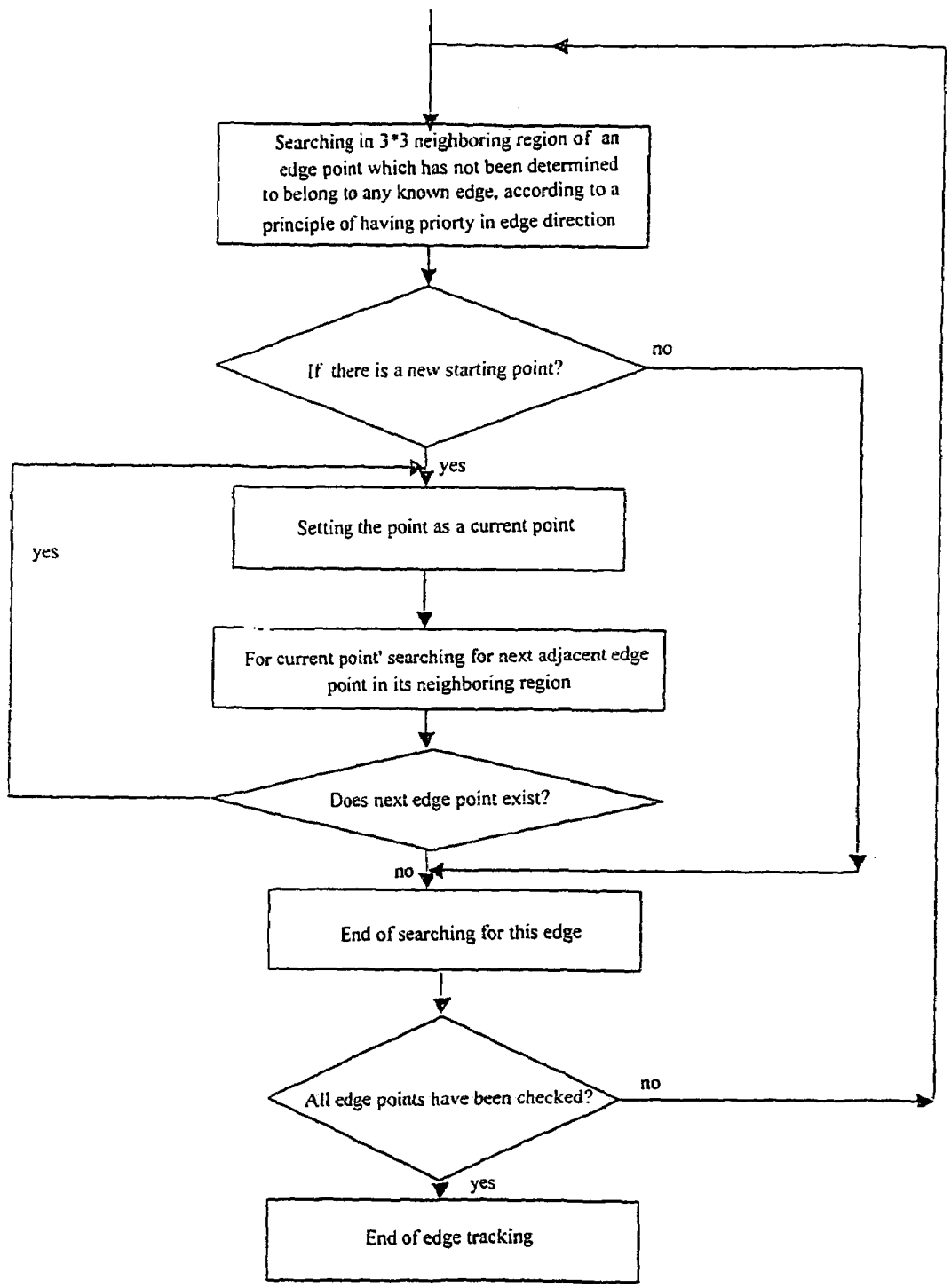
FIG. 3 is a flow-chart showing the steps of the edge tracking operation in accordance with present invention.
Figure 4:
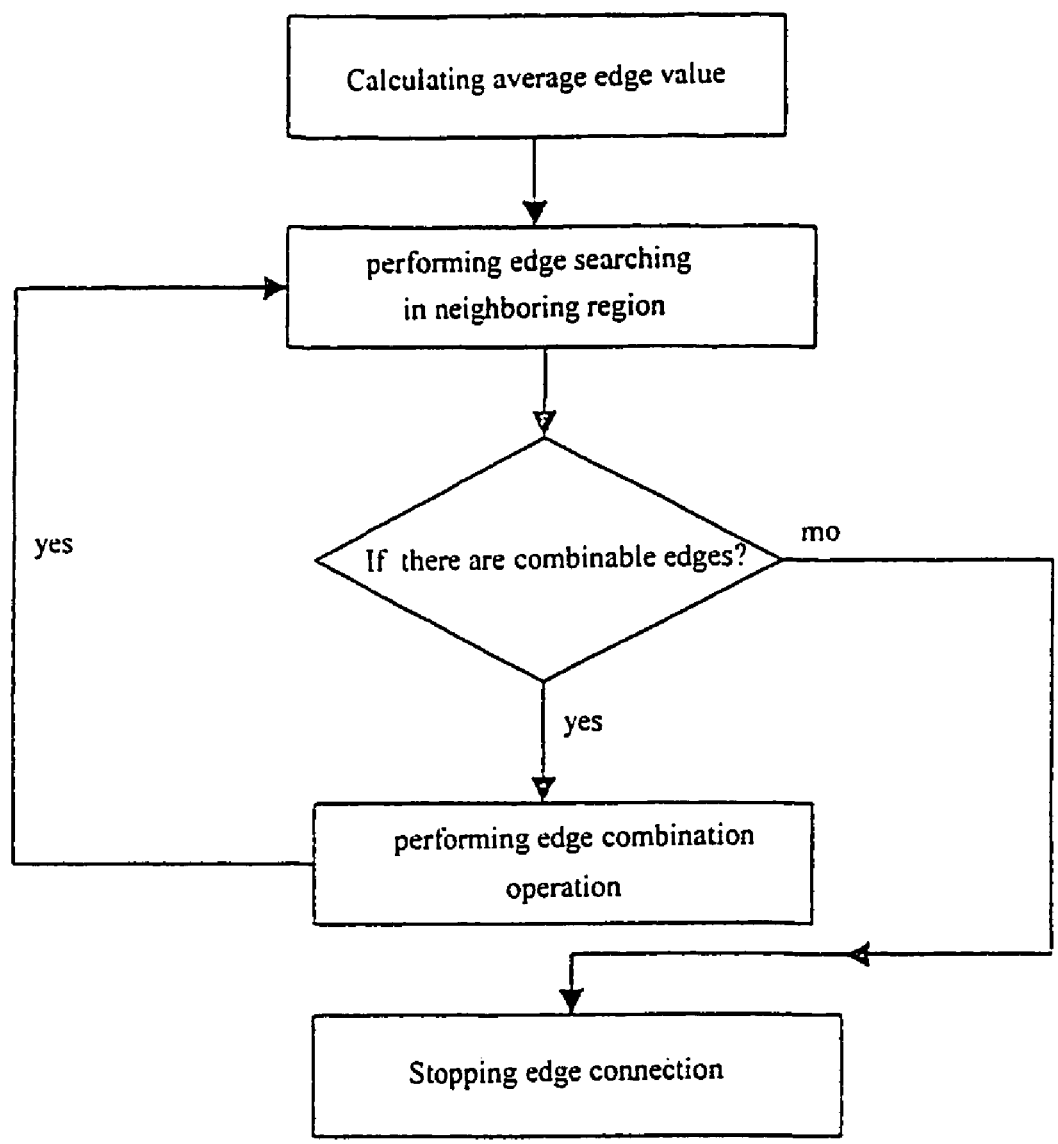
FIG. 4 is flow-chart showing the steps of the edge connection operation in accordance with present invention.

The process in step (5) includes: performing an edge tracking based on the edge value image EN (x,y) and the edge direction image D (x,y), calculating an average value for each edge segment obtained by the edge tracking operation, for each edge point on each edge segment, searching other edge points on other neighboring edge segments; if such an edge point is found, calculating a difference between the average edge values of the two edge segments; when the difference is located within a preset narrow range, determining logically the two edge segments to belong to a same edge. Refer to FIG. 3 illustrating a method for performing said edge tracking in step (5), the method includes the following steps: 1) for each edge point which has not been determined to belong to any known edge, searching one or more edge points in its 3*3 neighboring region based on a principle of having priority in edge direction, and if an edge point searched which has such an edge value that the difference between the value of said each edge point and the edge value of said edge point is located within a preset narrow range, and does not belong to any known edge is found, then determining these two points belong to a new edge and taking this point searched as a new starting point, while if no new starting point is found after all points have been searched, then stopping the edge tracking operation; 2) setting the new starting point as a current point, by using a method similar to that in step 1), searching for a next adjacent edge point in its neighboring regions being 3*3, 5*5, till 7*7, if the next adjacent edge point is found, taking it as the current edge point and repeating step 2), and if no such a point is found, then the searching operation for current edge is ended and turning to step 1) to search a next edge. Refer to FIG. 4 illustrating a method for performing said edge connection in step (5), the method includes the searching in neighboring regions being 3*3, 5*5, till 9*9 for each edge point, if it is found that a point belongs to another edge and the difference between the average edge values of the both edges is located within a preset narrow range, then the both edges belong to a same object, so combining the both edges and calculating an average edge value of the new edge; 3) After the searching operation for all points is ended, if any edge combination occurs, then repeating step 2), otherwise stopping the edge connection operation.

Then, the process in step (6) includes, for each edge point on the edge segments logically determined to belong to a same edge, searching for its adjacent points at the edge segments logically determined to belong to a same edge, and if there is one or more gaps between the edge point and its adjacent points, filling the gaps among them to close the edge.

The process in step (7) includes, for all points in the image, determining if a point belongs to that object, and marking all points belonging to the object, that is, region filling operation. The criterion for the determination here may be that for all points in the image, checking that if a point being at a same object edge in all 4 directions of top, down, left and right of a point exists, and if so, then the point is determined to belong to the same object Then the process in step (8) includes; cutting off false filled-regions, and this operation may be performed by using a region growing method.

At last, the process in step (9) includes combining a closed edge and some filling points to form a region as an independent object. This region can thus be shown distinctly to be recognized more easily.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

The invention claimed is:

1. An image segmentation recognition method in industrial radiational imaging, the method comprises the steps of:
   (1) Pre-processing an original image to reduce the influence of noises, denoting a gray level value of a pixel at (x,y) with G(x,y);
   (2) Log-transforming the image pre-processed to obtain a linear attenuation coefficient image, that is, A (x, y)=C In (G (x, y)/Io)+Ao, where Io=Ao is the maximum gray level value of the image, C is a constant used for adjusting the contrast;
   (3) Performing an edge detection on the linear attenuation coefficient image A (x, y) to obtain an edge value image E (x, y) and an edge direction image D (x, y);
   (4) Refining the edges by using the edge value image E (x, y) and edge direction image D (x, y), to create a new edge value image EN (x, y);
   (5) Performing an edge tracking operation by using the edge value image EN(x,y) and edge direction image D(x,y), calculating an average value for each edge segment obtained by the edge tracking operation, for each edge point on each edge segment, searching other edge points on other neighboring edge segments; if such an edge point is found, calculating a difference between the average edge values of the two edge segments; when the difference is located within a preset narrow range, determining logically the two edge segments to belong to a same edge;
   (6) For each edge point, on the edge segments logically determined to belong to a same edge searching for its adjacent points on the edge segments logically determined to belong to a same edge and if there is one or more gaps between the edge point and its adjacent points, filling the gaps to close the edge, thus forming a complete contour of an object;
   (7) Checking whether all points in the image belong to the object, and marking all points belonging to the object, filling the region;
   (8) Cutting off false filled-regions; and
   (9) Creating a region as an isolated object by combining a closed edge and filling points.

2. The image segmentation recognition method in industrial radiational imaging according to claim 1, wherein said pre-processing for an original image in step (1) may be performed using a Gaussian low-pass filtering in spatial domain.

3. The image segmentation recognition method in industrial radiational imaging according to claim 1, wherein the process for cutting off false filled regions in step (8) may be performed by using a method of region growing.

4. The image segmentation recognition method in industrial radiational imaging according to claim 1, wherein the criterion for said checking in step (7) may be that all points in the image are checked and if checked edge points of a same object exist in all 4 directions of top, down, left and right of a point, then the checked point is determined to belong to the object.

5. The image segmentation recognition method in industrial radiational imaging according to claim 1, wherein said process for edge detection in step (3) includes the following steps:
   at a 3*3 neighboring region of each candidate pixel (x, y), find out gradient values in 8 directions respectively by using a kirsh operator, the maximum gradient value therein is the edge value E(x,y) at that pixel, and the corresponding direction thereof is the edge direction D(x,y).

6. The image segmentation recognition method in industrial radiational imaging according to claim 1, wherein said process for refining the edges in step (4) comprises the steps of:
   1) Initial refining, that is by finding out peak value points on the edge value image to create a new edge value image E' (x, y);
   2) Further refining the initial refined edge value image E' (x, y) based on an iteration algorithm for sequential morphological refining, to erase redundant edge points repeatedly in 8 directions of east, south-east, south, south-west, west, north-west, north, and north-east, until the image can not be further refined, and thus to create a new edge value image EN (x, y).

7. The image segmentation recognition method in industrial radiational imaging according to claim 1, wherein the process for edge tracking in step (5) comprises the following steps:
   1) For each edge point which has not been determined to belong to any known edge, searching one or more edge points in its 3*3 neighboring region according to a principle of having priority in edge direction, and if an edge point searched which has such an edge value that the difference between the value of said each edge point and the edge value is located within a preset narrow range and does not belong to any known edge is found, then determining these two points belong to a new edge and taking this point searched as a new starting point, while if no new starting point is found when all points have been searched, then stopping the edge tracking operation;
   2) Setting the new starting point as a current edge point, by using a method similar to that in step 1), searching for a next adjacent edge point in its neighboring regions being 3*3, 5*5 till 7*7, and if the next adjacent edge point is found, taking it as the current edge point and repeating step 2), while if no such a point is found, then the searching operation for current edge is ended and turning to step 1) to search a next edge.

8. The image segmentation recognition method in industrial radiational imaging according to claim 1, wherein the process for edge connection in step (5) comprises the following steps:
   1) Calculating an average edge value for each edge;
   2) Searching in neighboring regions being 3*3, 5*5, till 9*9 for each edge point, if it is found that a point belongs to another edge and the difference between the average edge values of the two edges is located within a preset narrow range, then the two edges belong to a same object, so perfonning an edge combination operation to obtain a new edge and calculating an average edge value of the new edge; and
   3) After the searching operation for all points is ended, and if any edge combination occurs, then repeating step 2), otherwise stopping the edge connection operation.

* * * * *

UNITED STATES PATENT AND TRADEMARK OFFICE
CERTIFICATE OF CORRECTION

PATENT NO.        : 7,162,089 B2                                             Page 1 of 1
APPLICATION NO.   : 10/297845
DATED             : January 9, 2007
INVENTOR(S)       : Hui Jin et al.

It is certified that error appears in the above-identified patent and that said Letters Patent is hereby corrected as shown below:

On the Title Page of the Patent, please insert the following item and information between item numbers (22) and (86):

--(30) Foreign Application Priority Data

April 12, 2001           (CN).......................01110623.9--

Signed and Sealed this

Eighteenth Day of March, 2008

JON W. DUDAS
*Director of the United States Patent and Trademark Office*